United States Patent [19]
Scott et al.

[11] Patent Number: 5,348,871
[45] Date of Patent: Sep. 20, 1994

[54] PROCESS FOR CONVERTING CELLULOSIC MATERIALS INTO FUELS AND CHEMICALS

[75] Inventors: Charles D. Scott, Oak Ridge; Brendlyn D. Faison; Brian H. Davison, both of Knoxville; Jonathan Woodward, Oak Ridge, all of Tenn.

[73] Assignee: Martin Marietta Energy Systems, Inc., Oak Ridge, Tenn.

[21] Appl. No.: 884,506

[22] Filed: May 15, 1992

[51] Int. Cl.$^5$ .......................... C12S 1/00; C12P 7/10; C12P 7/06; C12N 9/42
[52] U.S. Cl. ........................ 435/165; 435/161; 435/162; 435/262; 435/276; 435/209; 435/105; 435/288; 435/813; 422/140; 422/234; 422/225
[58] Field of Search ............... 435/262, 161, 209, 100, 435/105, 874, 945, 267, 277, 182, 288, 813, 276, 162, 163, 165; 422/140, 234, 225

[56] References Cited

U.S. PATENT DOCUMENTS

| | | | |
|---|---|---|---|
| 3,642,580 | 2/1972 | Ghose | 195/33 |
| 3,765,475 | 10/1973 | Mandels et al. | 195/33 |
| 3,966,543 | 6/1976 | Cayle et al. | 162/158 |
| 3,972,775 | 8/1976 | Wilke et al. | 195/33 |
| 3,990,945 | 11/1976 | Huff et al. | 195/33 |
| 4,009,075 | 2/1977 | Hoge | 195/33 |
| 4,220,721 | 9/1980 | Emert et al. | 435/161 |
| 4,281,063 | 7/1981 | Tsao et al. | 435/99 |
| 4,321,328 | 3/1982 | Hoge | 435/165 |
| 4,326,032 | 4/1982 | Grove | 435/148 |
| 4,338,399 | 7/1982 | Weil et al. | 435/99 |
| 4,342,831 | 8/1982 | Faber et al. | 435/163 |
| 4,425,433 | 1/1984 | Neves | 435/163 |
| 4,440,904 | 6/1984 | Woodward | 435/165 |
| 4,447,534 | 5/1984 | Moebus et al. | 435/161 |
| 4,472,501 | 9/1984 | Takasawa et al. | 435/165 |
| 4,487,831 | 12/1984 | Day et al. | 435/815 |
| 4,564,595 | 2/1986 | Neves | 435/163 |
| 4,612,286 | 9/1986 | Sherman et al. | 435/137 |
| 4,713,334 | 12/1987 | Fujishima et al. | 435/99 |
| 4,840,903 | 6/1989 | Wu | 435/165 |
| 4,845,033 | 4/1989 | Tegtmeier | 435/162 |
| 4,933,283 | 6/1990 | Chen et al. | 435/166 |
| 4,978,647 | 12/1990 | Scott et al. | 502/7 |
| 4,995,985 | 2/1991 | Scott et al. | 210/679 |
| 5,248,484 | 9/1993 | Scott et al. | 422/225 |
| 5,270,189 | 12/1993 | Scott | 422/140 |

OTHER PUBLICATIONS

Wilke, C. R. et al., Preliminary Cost Analyses for Enzymatic Hydrolysis of Newsprint, Biotechnol. & Bioeng, Symp. No. 6, 155–175 (1976).

Scott, C. D. et al., Tapered Fluidized Bed Bioreactors For Environmental Control and Fuel Production, Advances in Biotechnology, International Fermentation Symposium No. 6 (London, Ontario), 651–656 (1981).

Scott, C. D. et al., Fixed-Bed, Anaerobic Treatment of Wastewater for Energy Conservation and Methane Production, Proceedings of the 16th Intersociety Energy Conversion Engineering Conference, 583–585 (1981).

(List continued on next page.)

Primary Examiner—Michael G. Wityshyn
Assistant Examiner—T. J. Reardon
Attorney, Agent, or Firm—Preston H. Smirman; Joseph A. Marasco; Harold W. Adams

[57] ABSTRACT

A process for converting cellulosic materials, such as waste paper, into fuels and chemicals utilizing enzymatic hydrolysis of the major constituent of paper, cellulose. A waste paper slurry is contacted by cellulase in an agitated hydrolyzer. The cellulase is produced from a continuous, columnar, fluidized-bed bioreactor utilizing immobilized microorganisms. An attritor and a cellobiase reactor are coupled to the agitated hydrolyzer to improve reaction efficiency. The cellulase is recycled by an adsorption process. The resulting crude sugars are converted to dilute product in a fluidized-bed bioreactor utilizing microorganisms. The dilute product is concentrated and purified by utilizing distillation and/or a biparticle fluidized-bed bioreactor system.

9 Claims, 1 Drawing Sheet

OTHER PUBLICATIONS

Scott, C. D. et al., Novel Developments in Bioreactor Design and Separations Technology, in Energy Applications of Biomass, M. Z. Lowenstein, Ed., Elsevier Applied Science, New York, 253–262 (1984).

Wright, J. D. et al., Design and Parametric Evaluation of an Enzymatic Hydrolysis Process (Separate Hydrolysis and Fermentation), Biotechnology and Bioengineering Symp. No. 17, 287–302 (1986).

Davison, B. H. et al., Ethanol Production From An Industrial Feedstock by Immobilized *Zymomonas mobilis* in a Fluidized-Bed Bioreactor, Biotechnology and Bioengineering Symp. No. 17, 629–632 (1986).

Scott, C. D., Dispersed-Phase Adsorbents for Biotechnology Applications, presented at the 2nd Internationl Conference on Separation Technology, Klais, FRG, 1–9 (1987).

Worden, R. M. et al., Dynamics of a Biological Fixed Film for Phenol Degradation in a Fluidized-Bed Bioreactor, Biotechnology and Bioengineering, vol. 30, 398–412 (1987).

Scott, C. D., Techniques for Producing Monodispersed Biocatalyst Beads for Use in Columnar Bioreactors, Annals of the New York Academy of Sciences, vol. 501, 487–493 (1987).

Wright, J. D., Ethanol from Biomass by Enzymatic Hydrolysis, Chemical Engineering Progress, 62–74 (Aug. 1988).

Davison, B. H. et al., Operability and Feasibility of Ethanol Production by Immobolized *Zymomonas mobilis* in a Fluidized-Bed Bioreactor, Appl. Biochem. Biotech., vol. 18, 19–34 (1988).

Woodward, Jonathan et al., Hydrolysis of Cellulose by Saturating and Non-Saturating Concentrations of Cellulase: Implications for Synergism, Bio/Technology, vol. 6, 301–304 (Mar. 1988).

Jones, E. O., et al., Kinetic Analysis of Bioconversion of Cellulose in Attrition Bioreactor, Biotechnology and Bioengineering, vol. 31, 35–40 (1988).

Scott, C. D. et al., Solute Diffusion in Biocatalyst Gel Beads Containing Biocatalysis and Other Additives, Enzyme Microb. Technol., vol. 11, 258–263 (May 1989).

Watson, J. S., et al., Adsorption of Sr by Immobolized Microorganisms, Applied Biochemistry and Biotechnology, vol. 20/21, 699–709 (1989).

Petersen, J. N. et al., Accumulation of $Cu^{++}$ Onto Modified Bone-Gelatin Beads, Biotechnology Techniques, vol. 4, No. 6, 435–440 (1990).

Wilkins, E. et al., Performance of Immobilized Enzyme on Saccharification and Fermentaion of Agricultural Wastes and Wood Residues, J. Environ. Sci. Health, vol. A26, No. 6, 883–898 (1991).

Davison, B. H. et al., Simultaneous Fermentation and Separation of Lactic Acid in a Bioparticle Fluidized-Bed Bioreactor, Applied Biochemistry and Biotechnology, vol. 34/35, 431–439 (1992).

Davison, B. H. et al., A Proposed Bioparticle Fluidized-Bed for Lactic Acid Fermenation and Simultaneous Adsorption, Biotechnology and Bioengineering, vol. 39, 365–368 (1992).

Crueger et al. "Biotechnology: A Textbook of Industrial Microbiology", Sinauer Assoc., Sundenland, Mass. 1982 pp. 278–280.

PROCESS FOR CONVERTING CELLULOSIC MATERIALS INTO FUELS AND CHEMICALS

This invention was made with Government support under Contract No. DE-AC05-84OR21400 awarded by the U.S. Department of Energy to Martin Marietta Energy Systems, Inc. and the Government has certain rights in this invention. This invention was funded through the Office of Conservation and Renewable Energy.

FIELD OF THE INVENTION

This invention relates to the conversion of solid wastes, such as cellulosic materials, into fuels and chemicals, and more particularly to a bioprocessing system employing enzymatic hydrolysis of the major constituent of paper, cellulose, into sugar and subsequent bioconversion of the sugar to fuels or chemicals using advanced bioreactor concepts.

BACKGROUND OF THE INVENTION

Waste materials, particularly solid wastes, from various sources are continuing to increase at the same time that disposal of such material is becoming more difficult and expensive. As a result, there is increasing interest in recycling useful components of wastes and in using certain fractions for production of energy or higher-value materials such as useful chemicals. The growing interest in segregation of solid waste, frequently at the source, will potentially provide relatively well-defined materials that are prime candidates for other uses. Of particular interest is the large amount of cellulosic materials, already segregated, that could be considered as low-cost, perhaps even negative cost, feed materials for the production of crude sugars and various other useful chemicals such as alcohols, neutral solvents and organic acids. Cellulosic materials are defined as those materials which contain cellulose. Cellulosic materials include wood, woody pulp, woody biomass, paper and cardboard and related materials. As a result of using these materials as a useful chemical feed material the problem of disposal of solid wastes would be partially alleviated.

Solid waste material from residential and industrial sources represent a heterogenous mixture that is predominantly made up of metals, glass, plastics, food residues, and paper products. Although conservation efforts have had a significant impact, the volume of this material remains quite large and will probably continue to increase in the foreseeable future. A large amount of this material is either deposited in landfills or incinerated, whereas only a small amount is recycled or further used. Due to environmental restrictions and a lack of suitable new sites, disposal by landfill or incineration is becoming prohibitively expensive or even impossible in certain areas.

It has been estimated that half of municipal solid waste is made up of paper, with the other half consisting of glass, plastics, metals and other materials. A significant portion of the waste paper is comprised of newsprint. Large fractions of various types of the solid waste materials could be effectively recycled if fractionation and segregation of the components was carried out. Although there is some technology available that will fractionate mixed waste, there appears to be a trend towards segregation by the generator. If this occurs on a large scale, materials that are not readily recycled could well be considered as relatively well-defined feed materials for further processing.

Segregated waste paper products could be an ideal feed material for biological conversion to sugars (conversion of cellulose and hemicellulose) or aromatic compounds (conversion of lignin) with the possibility of subsequent conversion to a variety of useful chemicals. Of particular interest would be the production of organic acids, neutral solvents and various alcohols as fuels or chemical intermediates.

Waste paper is made up of three primary constituents: cellulose (~61%), hemicellulose (~16%), and lignin (~21%). The first two, cellulose and hemicellulose, are complex carbohydrates that can be hydrolyzed to the monomer sugars, glucose and xylose by use of the appropriate enzyme systems. The primary sugar is glucose which represents an intermediate product that can also be converted to chemicals such as ethanol by a fermentation process. The process chemistry of interest is listed below:

Over-all Cellulose Hydrolysis to Glucose

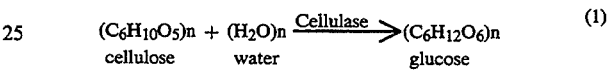

Cellobiose Formation (an inhibiting intermediate product)

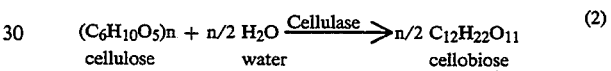

Hydrolysis of Cellobiose to Glucose

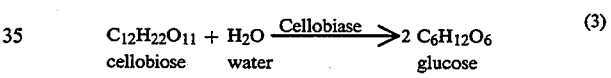

Bioconversion of Glucose to Ethanol

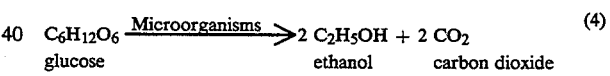

Unless extensive purification is carried out, the usual cellulase enzymes (a crude extract from specific microorganisms) include a mixture that has several functions including those biocatalysts that interact with the internal members of the cellulose polymer and those that interact with the end groups. Cellobiose, an intermediate disaccharide, that is also formed (Equation 2), inhibits the hydrolysis reaction. Cellobiose can be converted to glucose if a sufficient quantity of the enzyme cellobiase is present (Equation 3). Cellobiase is also a constituent of the crude mixture of the cellulase enzymes but it is usually present at a relatively low concentration. In order to enhance the overall hydrolysis process, exposure to additional cellobiase would be highly beneficial. Lignin is a polymeric structure of aromatic compounds which can be oxidized to a series of useful chemical compounds, but this technology is not well-developed as yet, so that residue could be used as a fuel for producing steam.

Research on saccharification processes for the conversion of cellulose to glucose have taken two major approaches. Acid hydrolysis is attractive since it is relatively rapid. However, the acid processes also produce chemicals other than sugar that represent a process loss or complication. Treating the acid effluent or recovery of the excess acid also presents problems. On the other hand, the enzymatic approach is much more specific with a higher yield but, until recently, there has been concern over the length of time for the reaction and the potential high cost of the biocatalyst since there was no processing scheme for recovery and reuse. Both of the shortcomings of the enzyme process can be alleviated making it the obvious choice for new process development. The bioprocessing system of the present application is centered around the enzymatic hydrolysis of a major fraction of the cellulose in paper by the use of cellulases isolated from selected fungi. This will be followed by the subsequent fermentation of the resulting sugars to chemicals with a preliminary emphasis on useful chemicals such as ethanol.

OBJECTS OF THE INVENTION

Accordingly, it is an object of the present invention to provide a new and improved process for recycling cellulosic materials.

It is another object of the present invention to provide a new and improved process for producing fuels and chemicals, such as ethanol.

It is another object of the present invention to provide a new and improved process for reducing the cost of solid waste disposal.

Further and other objects of the present inventions will become apparent from the description contained herein.

SUMMARY OF THE INVENTION

In accordance with one aspect of the present invention, the foregoing and other objects are achieved by:

(a) size-reducing the cellulosic material;

(b) mixing the size-reduced cellulosic material with a sufficient amount of water to form a slurry;

(c) introducing the slurry into a reaction vessel;

(d) introducing cellulase into the reaction vessel so that the cellulase contacts the slurry so that a hydrolysis reaction occurs, the hydrolysis reaction forming sugar and cellobiose;

(e) circulating the reactants through an attritor and a cellobiase reactor;

(f) recovering from the reaction vessel a hydrolysis product stream, the hydrolysis product stream containing sugar and cellulase;

(g) recovering and recycling the cellulase of the hydrolysis product stream;

(h) converting the sugar of the hydrolysis product stream to a dilute product; and (i) concentrating and purifying the dilute product into an end product.

DETAILED DESCRIPTION OF THE PREFERRED EMBODIMENTS

Figure 1:
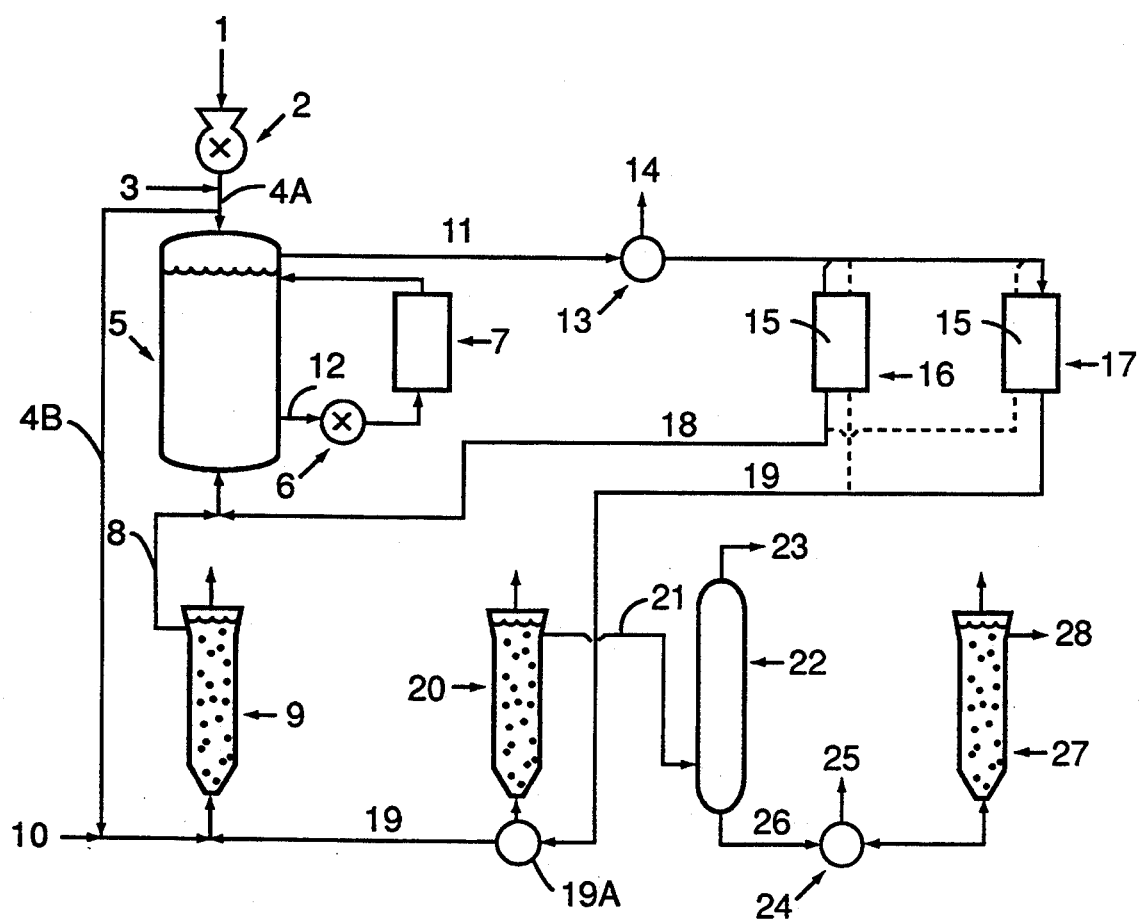
FIG. 1 is a schematic diagram of the major processing steps involved with the conversion of cellulosic materials into fuels and chemicals, in accordance with the present invention.

With reference to FIG. 1, the cellulosic material 1 is placed into a shredder 2. Several adequate shredding systems covering a wide size range are available on the market such as the Paper Disintegrator manufactured by Jay Bee Manufacturing, Inc., Tyler, Tex. Size reduction of the cellulosic material 1 and the formation of a thick aqueous slurry 4a (pulping) will be required for further processing. The formation of a thick aqueous slurry 4a is accomplished by mixing the shredded cellulosic material 1 with makeup water 3.

The slurry 4a is then added to an agitated hydrolyzer 5, where it is contacted by the crude cellulase 8. The agitated hydrolyzer 5 is usually operated according to the following parameters: a temperature in the range of about 40° to about 60° C., a crude cellulase concentration in the range of about 1 to about 100 international units, (1 international unit (I.U.) is defined as 1 $\mu$mole/minute of glucose equivalent released) and a paper pulp concentration in the range of about 1 to about 20 wt.%. Rather than using a conventional batch-fed stirred tank for the bioreactor, the crude cellulase 8 is produced from a continuous, columnar, fluidized-bed bioreactor 9 utilizing immobilized fungi such as *Trichoderma reesei*, for example. A portion of the slurry 4b is diverted and combined with required nutrients 10 and introduced into the fluidized-bed bioreactor 9 in order to produce the crude cellulase 8. Additionally, a portion of the crude sugars 19 produced from the hydrolysis reaction is used to induce secretion of the cellulase after which it can be collected by ultrafiltration by utilizing an ultrafilter 17A, for example. Although the present invention utilizes a system for the production of the crude cellulase 8, commercially available cellulase can also be used to hydrolyze the cellulose. The fluidized bed bioreactor 9 is usually operated according to the following parameters: a temperature in the range of about 25° to about 33° C., a glucose concentration in the range of about 0.1 to about 1.0%, and a fluidizing velocity in the range of about 0.1 to about 1.0 cm/sec. The slurry 4a is contacted with the crude cellulase 8 in the agitated hydrolyzer 5 for an adequate amount of time for saccharification, and hence solubilization, to occur. In the past, such systems were designed as simple, batch-fed, stirred tanks. Reaction times of many hours or even days were required for an acceptable yield. There are two basic problems that must be overcome in order to enhance this processing step. First, part of the enzyme process generally requires fresh surface area in order to maintain a high rate of reaction. Secondly, one of the intermediate products, cellobiose (a disaccharide), inhibits the further breakdown of paper to cellulose. An attritor 6, in fluid communication with the agitated hydrolyzer 5, is used in order to constantly provide new surface area and increase the reaction efficiency. This is accomplished by introducing a hydrolyzer side stream 12 into the attritor 6. The attritor 6 can be comprised of any means which produces a high-shear field for causing attrition or size reduction of the solid particulate. For many applications, the attritor 6 can be comprised of a high speed rotor contained in an enclosed chamber through which the slurry passes. In many cases, a high-speed centrifugal pump can be used for this purpose. For large or particularly hard particulates, a grinder, shredder, blender, or other size reduction device may be utilized in place of, or in addition to, the pump. In any case, means to circulate the reactor contents through the attritor 6 can be provided by the attritor 6 itself, or by separate circulating means, such as a diaphragm pump or other type of pump. The attritor 6 may comprise several devices in series, parallel, or complex configurations. Since the attritor 6 also mixes and circulates the reactants, a stirring device may be optional. The attritor 6 may be operated constantly or intermittently. A complete description of this technology is found in U.S. Pat. No. 5,248,484 to Scott et al., the entire disclosure of which is incorporated herein by reference.

The effects of cellobiose inhibition are reduced by coupling a cellobiase reactor 7 to the agitated hydrolyzer 5. After the hydrolyzer side stream 12 passes through the attritor 6 it is then preferably introduced into the cellobiase reactor 7. Such an approach can be most effectively accomplished by using a fixed-bed of immobilized cellobiase through which a hydrolyzer side stream 12 is directed prior to recycle back to the agitated hydrolyzer 5. The cellobiase can be immobilized by adsorption of a dispersed sorbent in a stabilized gel bead. The immobilized cellobiase can effectively reduce the level of cellobiose for extended periods without replenishment. The use of the cellobiase reactor 7 is more efficient than adding the cellobiase enzyme in free suspension into the hydrolysis reactor where it will ultimately be lost during recycle and reuse. The attritor 6 and the cellobiase reactor 7 can be in fluid communication with the agitated hydrolyzer 5 in either a series or parallel configuration.

The hydrolysis product stream 11 is passed through a filter 13 to remove any waste solids 14 that may be present. After the hydrolysis product stream 11 has been filtered, an enzyme recovery and reuse system for enzyme adsorption and recycle is used to allow up to 80% recycle of the cellulase. A sorbent 15 is used to remove the cellulase from the hydrolysis product stream 11 prior to further conversion of the crude sugars 19 to chemicals. Cellulosic material, in the form of paper, for example, could be the most useful sorbent in such a process. In a preferred embodiment, the hydrolysis product stream 11 is contacted with the sorbent 15, such as DEAE-Macrosorb ™, available from Sterling Organics, Rensselaer, N.Y., at a basic pH, thereby resulting in the adsorption of cellulase on the sorbent 15. The cellulase-sorbent complex is then contacted with a solution having an acidic pH to release the cellulase from the sorbent 15. A complete description of this process is found in U.S. Pat. No. 4,840,904 to Woodward, the entire disclosure of which is incorporated herein by reference. The resulting recycle cellulase 18 is then reintroduced into the agitated hydrolyzer 5 for further processing of additional slurry 4a, while the resulting crude sugars 19 are ready for fermentation. It is convenient to employ the cellulase sorbent 15 in multiple fixed-bed enzyme sorbers 16, 17 that can be alternately active and regenerated.

Fermentation of the crude sugars 19 to ethanol 23 or other chemicals is carried out in an fluidized-bed bioreactor 20 utilizing immobilized microorganisms at high concentration. If the product is to be ethanol 23, then immobilization of the microorganism *Zymomonas mobilis* at concentrations greater than $10^{10}$ cells per mL would be used. Immobilization material could be either cross-linked carrageenan or chemically-modified bone gel in 1.0 to 1.5 ram-diameter gel beads. A complete description of this technology is found in U.S. Pat. Nos. 4,978,647 and 4,995,985, both to Scott et al., the entire disclosures of which are incorporated herein by reference. The fluidized bed bioreactor 20 is usually operated according to the following parameters: a temperature in the range of about 25° to about 40° C., a sugar concentration in the range of about 5 to about 20%, and a liquid flow velocity in the range of about 0.1 to about 1.0 cm/sec. The resulting $CO_2$ from this fermentation could be recovered as a useful byproduct. Additionally, incorporation of a concentration step based on adsorption may also be considered. In the case of adsorption, a compatible solid sorbent could be used that has a high affinity for the end product. This can be accomplished by the utilization of a biparticle fluidized-bed bioreactor that allows for the combination of both fermentation and product recovery by sorbent particles moving cocurrently or countercurrently through a fluidized bed of biocatalyst particles. A complete description of this process is found in U.S. Pat. No. 5,270,189 to Scott et al., the entire disclosure of which is incorporated herein by reference. An example of ethanol production in accordance with the present invention is presented below:

EXAMPLE I

The process described herein is suitable for the enhanced production and recovery of ethanol. *Zymomonas mobilis*, a bacterium, is immobilized in 4% carrageenan beads. The feed is 15% dextrose solution made from corn syrup and light steep water with 0.05 M KCl and antifoam added. In a 3-in.-ID column the flowrate is approximately 10 L/h. The optimum process temperature is about 30° to 35° C. A sorbent second particulate phrase, such as a polystyrene resin or a hydrophobic molecular sieve such as Linde SILICALITE ™ is added and removed continuously in accordance with the present invention to recover the ethanol product and prevent inhibitory buildup of the product in the reactor.

In the alternative, concentration and purification of the end product can be accomplished by relatively conventional distillation utilizing a distillation still 22, for example. In another embodiment in accordance with the present invention, the dilute product can be concentrated and purified by utilizing a contactor. The contactor would contain a sorbent having a high affinity for the dilute product. The dilute product is introduced into the contactor containing an appropriate sorbent, the sorbent sorbs the dilute product, thereby resulting in concentration and purification of the dilute product into an end product, which is then recovered. The contactor can be either the fluidized-bed or fixed-bed type. Additionally, the contactor can be arranged in a multiple configuration, with one or more contactors being active and regenerated.

Although this bioprocessing system is expected to have minimal impact on the environment, there will generally be a waste water stream 26 containing carbonaceous material that is preferably removed or treated before release or recycle of the waste water stream 26. A filter 24 can remove waste solids 25 before further processing of the waste water stream 26. After the waste water stream 26 is filtered it is introduced into a fluidized-bed bioreactor 27 with immobilized biodegrading biocatalysts. The fluidized-bed bioreactor is usually operated according to the following parameters: a temperature; in the range of about 22° to about 38° C., and a feed rate in the range of about 0.2 ml/$cm^2$-min. to about 58.7 ml/$cm^2$-min. Immobilization of the biocatalysts is achieved by utilizing gel beads or granular particles. The biocatalysts could be any species of bacteria belonging to the genus Pseudomonas. Generally, these bacteria are present in concentrations of about $10^9$ to about $10^{11}$ organisms/ml. Additionally, the biocatalysts can be selected from the methanogens. The biocatalysts are capable of degrading the carbonaceous material, usually present in the waste water stream at a level of about 10 to about 1000 parts per million, so that there is a 90% carbonaceous material removal rate. The resulting water stream 28 is then discharged or recycled.

While there has been shown and described what are at present considered the preferred embodiments of the invention, it will be obvious to those skilled in the art that various changes and modifications can be made therein without departing from the scope of the inventions defined by the appended claims.

What is claimed is:

1. A process for converting cellulosic material into glucose and ethanol comprising the steps of:

shredding a cellulosic material to increase the surface area of the cellulosic material;

mixing the shredded cellulosic material with a sufficient amount of water to form a slurry;

introducing the slurry into a first reaction vessel;

introducing cellulase into the first reaction vessel under conditions suitable to cause a hydrolysis reaction of the cellulose, the hydrolysis reaction forming glucose and cellobiose from the cellulose;

circulating the slurry from the first reaction vessel through an attritor and then through a cellobiase reactor and back to the first reaction vessel, the attritor comprising a centrifugal pump, the attritor being in fluid communication with the first reaction vessel, the cellobiase reactor comprising a fixed bed of immobilized cellobiase, the cellobiase reactor being in fluid communication with the attritor and the first reaction vessel, the attritor providing increased surface area to the cellulosic material, the cellobiase reactor providing continuous removal of cellobiose from the first reaction vessel;

recovering from the first reaction vessel a first hydrolysis product stream, the first hydrolysis product stream containing glucose, cellulase and particulate matter;

filtering the first hydrolysis product stream to remove particulate matter and to form a second hydrolysis product stream, the second hydrolysis product stream containing cellulase and glucose;

contacting a first sorbent with the second hydrolysis product stream at a basic pH to sorb the cellulase to form a cellulase-sorbent complex;

contacting the cellulase-sorbent complex with a solution having an acidic pH to separate the cellulase from the cellulase-sorbent complex;

returning the cellulase to the first reaction vessel;

fermenting the glucose of the second hydrolysis product stream to ethanol by action of a biocatalyst in a biparticle fluidized-bed bioreactor, the biparticle fluidized-bed bioreactor containing the biocatalyst and a second sorbent, the biocatalyst being *Zymomonas mobilis*, the ethanol being sorbed by the second sorbent to form an ethanol-sorbent complex; and desorbing the ethanol from the ethanol-sorbent complex.

2. The process of claim 1, wherein the cellulosic material is paper.

3. The process of claim 1, wherein the step of circulating the slurry through the attritor further comprises the steps of:

introducing the slurry into the attritor; and activating the attritor so that the slurry is circulated through the attritor so that the cellulosic material is attrited, thereby resulting in increased surface area of the cellulosic material where the hydrolysis reaction can occur.

4. The process of claim 1, wherein the step of circulating the slurry through the cellobiase reactor and removing the cellobiose further comprises the steps of:

introducing the slurry into the cellobiase reactor;

reacting the cellobiose with the cellobiase of the cellobiase reactor to form glucose; and returning the slurry and the glucose to the reaction vessel.

5. The process of claim 1, wherein the first sorbent is contained in at least one fixed-bed enzyme sorber.

6. The process of claim 1, wherein the biparticle fluidized-bed bioreactor comprises:

a second reaction vessel;

a fluid first phase flowing through the second reaction vessel, the fluid first phase comprising the second hydrolysis product stream;

a fluidized particulate second phase in the second reaction vessel, the second phase being retained within the second reaction vessel, the fluidized particulate phase comprising the biocatalyst; and a particulate third phase in the second reaction vessel, the third phase migrating through the second reaction vessel, the particulate third phase comprising the second sorbent.

7. The process of claim 5, wherein at least two fixed-bed enzyme sorbers are alternately active.

8. The process of claim 6, wherein the second sorbent flows cocurrently with respect to the fluid first phase.

9. The process of claim 6, wherein the second sorbent flows countercurrently with respect to the fluid first phase.

* * * * *